US005817635A

United States Patent [19]
Eckstein et al.

[11] Patent Number: 5,817,635
[45] Date of Patent: Oct. 6, 1998

[54] MODIFIED RIBOZYMES

[75] Inventors: Fritz Eckstein, Gottingen, Germany; Wolfgang Pieken, Boulder, Colo.; Fritz Benseler, Gleichen/Etzborn, Germany; David B. Olsen, West Point, Pa.; David M. Williams, Cherry Hinton, England; Olaf Heindenreich, Gottingen, Germany

[73] Assignee: Max-Planck-Gesellschaft zur Förderung der Wissenschaften e.V., Göttingen, Germany

[21] Appl. No.: 434,547

[22] Filed: May 4, 1995

Related U.S. Application Data

[62] Division of Ser. No. 965,411, Aug. 9, 1993.
[51] Int. Cl.$^6$ ............................. A61K 48/00; C12Q 1/68; C12N 15/85
[52] U.S. Cl. ............................ 514/44; 435/6; 435/91.31; 435/172.3; 435/320.1; 435/325; 435/366; 536/23.1; 536/23.2; 536/24.5
[58] Field of Search ......................... 435/6, 91.31, 172.3, 435/320.1; 514/14; 536/23.1, 23.2, 24.5

[56]  References Cited

U.S. PATENT DOCUMENTS

| | | | |
|---|---|---|---|
| 5,149,796 | 9/1992 | Rossi et al. | 536/23.2 |
| 5,298,612 | 3/1994 | Jennings et al. | 536/23.2 |
| 5,334,711 | 8/1994 | Sproat et al. | 536/24.5 |

FOREIGN PATENT DOCUMENTS

| | | |
|---|---|---|
| 0387775 | 9/1990 | European Pat. Off. . |
| 0321201 | 12/1994 | European Pat. Off. . |
| 8804300 | 6/1988 | WIPO . |
| 9103162 | 3/1991 | WIPO . |
| 9207065 | 4/1992 | WIPO . |

OTHER PUBLICATIONS

Stull et al., Pharm. Res. 12:465 (1995).
Baer et al., *Nucleic Acids and Molecular Biology*, vol. 3, pp. 231–250, Eckstein and Lilley eds, Springer Verlag, Berlin/Heidelberg (1988).
Bass and Cech, "Ribozyme Inhibitors: Deoxyguanosine and Dideoxyguanosine are Competitive Inhibitors of Self–Splicing of the Tetrahymena Ribosomal Ribonucleic Acid Precursor," *Biochemistry* 25:4473–4477 (1986).
Been and Cech, "One Binding Site Determines Sequence Specificity of Tetrahymena Pre–rRNA Self–Splicing, Trans–Splicing and RNA Enzyme Activity," *Cell* 47:207–216 (1986).
Black et al., *Virology* 48:537–545 (1972).
Cameron and Jennings, "Specific Gene Expression by Engineered Ribozymes in Monkey Cells," *Proc. Natl. Acad. Sci. USA* 86:9139–9143 (1989).
Cech, "A Model for the RNA–Catalyzed Replication of RNA," *Proc. Natl. Acad. Sci. USA*, 83: 4360–4363 (1986).
Cech, "RNA as an Enzyme," *Scientific American* 255:76–84 (1986).
Cech, "The Chemistry of Self–Splicing RNA and RNA Enzymes," *Science* 236:1532–1539 (1987).
Cech, "Self–Splicing of Group I Introns," *Ann. Rev. Biochem.* 59:543–568 (1990).
Cedergren et al., "Catalytic RNA as an Anti–HIV Agent: Design and Delivery to Cells," *Abstract NIH Conference* Oct. 21–24, 1990, San Diego, California.
Cedergren et al., Abstract presentation at Cold Spring Harbor meeting: RNA Processing, May 15–19, 1991.
Cedergren et al., Abstract presentation at Cold Spring Harbor meeting: RNA Processing, May 16–20, 1990.
Chowrira et al., "Four Ribose 2'–Hydroxyl Groups Essential for Catalytic Function of the Hairpin Ribozyme," *J. Biol. Chem.* 268:19458–19462 (1993).
Chowrira and Burke, "Binding and Cleavage of Nucleic Acids by the Hairpin Ribozyme," *Biochemistry* 30:8518 (1991).
Codington et al., *J. Org. Chem.* 29:558–567 (1964).
Cotten, "The in vivo application of ribozymes," *TIBS* 8:174–178 (1990).
Cotten et al., "Ribozyme, Antisense RNA, and Antisense DNA Inhibition of U7 Small Nuclear Ribonucleoprotein–Mediated Histone Pre–mRNA Processing In Vitro," *Mol. Cell. Biol.* 9:4479–4487 (1989).
Doerr & Fox, *J. Org. Chem.* 32:1462 (1976).
Doudna et al., "A Multisubunit that is a Catalyst of and Template for Complementary Strand RNA Synthesis," *Science* 251:1605 (1991).
Ellington and Szostak, *Nature* 346:818–822 (1990).
Engli et al., "Crystal Structure of an Okazaki Fragment at 2–A Resolution," *Proc. Natl. Acad. Sci. USA* 89:534–538 (1992).
Fedor and Uhlenbeck, "Substrate sequence effects on hammerhead RNA catalytic efficiency," *Proc. Natl. Acad. Sci. USA* 87:1668–1672 (1990).
Greider and Blackburn, *Nature* 337:331–337 (1989).
Hampel et al., "'Hairpin' Catalytic RNA Model: Evidence for Helices and Sequence Requirement for Substrate RNA," *Nucleic Acids Research* 18:299–304 (1990).
Haseloff and Gerlach, "Simple RNA Enzymes with New and Highly Specific Endoribonuclease Activities," *Nature* 334:585–591 (1988).
Herschlag and Cech, *Nature* 344:405–409 (1990).
Hobbs et al., *Biochemistry* 11:43367–4334 (1972).
Hobbs et al., *Biochemistry* 12:5138–5145 (1973).
Hutchins et al., "Self–cleavage of Plus and Minus RNA Transcripts of Avocado Sunblotch Viroid," *Nucleic Acids Research* 14:3627–3640 (1986).
Ikehara and Miki, *Chem. Pharm. Bull.* 26:2449–2453 (1978).

(List continued on next page.)

Primary Examiner—John L. LeGuyader
Attorney, Agent, or Firm—Lyon & Lyon LLP

[57]  ABSTRACT

The claimed invention is drawn to RNA molecules with catalytic activity comprising at least one modified nucleoside having a modifier group replacing the hydroxy group at the 2'-position of the ribose sugar where the modifier group is an halo, amino, mono- or disubstituted amino, or an azido group, and methods of use in vivo.

42 Claims, 9 Drawing Sheets

OTHER PUBLICATIONS

Imazawa and Eckstein, *J. Org. Chem.* 44:2039–2041 (1979).

Ludwig, "A New Route to Nucleoside 5'–Triphosphates," *Acta Biochim. Biophys. Acad. Sci. Hung.* 16:131–133 (1981).

Ludwig and Eckstein, "Rapid and Efficient Synthesis of Nucleoside 5'–O–(1–Thiotriphosphates), 5'–Triphosphates and 2',3'–Cyclophosphorothioates Using 2–Chloro–4H–1,3, 2–Benzodioxaphosphorin–4–one," *J. Org. Chem.* 54:631–635 (1989).

Mengel and Guschlbauer, *Ang. Chem.* 90:557–558 (1979).

Mungall et al., *J. Org. Chem.* 40:1659 (1975).

Nielsen et al., "Sequence–Selective Recognition of DNA by Strand Displacement with a Thymine–Substituted Polyamide," *Science* 254:1497 (1991).

Paolella et al., "Nuclease Resistant Ribozymes with High Catalytic Activity", *EMBO J.* 11:1913–1919 (1992).

Perreault et al., "Mixed Deoxyribo– and Ribo–Oligonucleotides with Catalytic Activity," *Nature* 344:565–567 (1990).

Perreault et al., "Relationship between 2'–Hydroxyls and Magensium Binding in the Hammerhead RNA Domain: A Model for Ribozyme Catalysis," *Biochemistry* 30:4020–4025 (1991).

Pieken et al., "Kinetic Characterization of Ribonuclease–Resistant 2'–Modified Hammerhead Ribozymes," *Science* 253:314–317 (1991).

Pieken et al., "Influence of 2'–Amino and 2'–Fluoro Modifications on the Catalytic Properties of Hammerhead Ribozymes," *Abstract of the 14th International tRNA workshop* May 4–9, 1991, Ridzyna, Poland.

Price and Cech, "Coupling of Tetrahymena Ribosomal RNA Splicing to β–Galactosidase Expression in *Esherichia coli*," *Science* 228:719 (1985).

Rossi and Sarver, "RNA enzymes, ribozymes as antiviral therapeutic agents," *TIBTECH* 8:179–183 (1990).

Ruffner et al., "Thiophosphate interference experiments locate phosphates important for the hammerhead RNA self–cleavage reaction," *Gene* 82:31–41 (1989).

Sarver et al., "Ribozymes as Potential Anti–HIV–1 Therapeutic Agents" *Science* 247:1222–1225 (1990).

Scaringe et al., "Chemical synthesis of biologically active oligoribonucleotides using β–cyanoethyl protected ribonucleoside phosphoramidites," *Nucl Acids Res.* 18:5433–5441 (1990).

Sheldon et al., *Nucleic Acids and Molecular Biology*, vol. 4., pp. 227–242, eds Eckstein and Lilley, Springer Verlag Berlin Heidelberg (1990).

Sinha et al., *Nucleic Acids Research* 12:4539–4577 (1984).

Strobel and Cech, "Tertiary Interactions with the Internal Guide Sequence Mediate Docking of the P1 Helix into the Catalytic Core of the T. Ribozyme," *Biochemistry* 32:13593 (1993).

Sung, *J. Org. Chem.* 47:3623–3628 (1982).

Symons, *TIBS* 14:445–450 (1989).

Tuerk and Gold, "Systematic Evolution of Ligands by Exponential Enrichment: RNA Ligands to Bacteriophage T4 DNA Polymerase," *Science* 249:505–510 (1990).

Uchida and Egami, *The Enzymes* vol. IV, 3rd ed., pp. 205–250, P.D. Boyer editor, Academic Press (1971).

Uhlenbeck, "A Small Catalytic Oligoribonucleotide," *Nature* 328:596–600 (1987).

Uhlenbeck, *Proc. Natl. Acad. Sci. USA* 87:1668–1672 (1990).

Uhlmann and Peyman, "Antisense Oligonucleotides: A New Therapeutic Principle," *Chemical Reviews* 90:544 (1990).

Verheyden et al., *J. Org. Chem.* 36:250 (1971).

Williams et al., "Properties of 2'–Fluorothymidine–Containing Oloigonucleotides: Interaction with Restriction Endonuclease EcoRV," *Biochemistry* 30:4001–4009 (1991).

Wu et al., "Convenient Procedure for the Preparation of Specific Mixed DNA–RNA Polymers," *J. Am. Chem. Soc.* 111:8531–8533 (1991).

Yang et al., "Minimum Ribonucleotide Requirement for Catalysis by the RNA Hammerhead Domain," *Biochemistry* 31:5005 (1992).

Yang et al., "Mixed DNA/RNA Polymers Are Cleaved by the Hammerhead Ribozyme," *Biochemistry* 29:1156 (1990).

Zang et al., *Biochemistry* 27:8924–8931 (1988).

Zaug and Cech, "The Intervening Sequence RNA of Tetrahymena Is a Enzyme," *Science* 231:470–475 (1986).

Zaug et al., "The Tetrahymena Ribozyme Acts Like an RNA Restriction Endonuclease," *Nature* 324:429434 (1986).

Zaug et al., "The Tetrahymena interventing sequence ribonucliec acid enzyme is a phosphotransferase and an acid phosphatase," *Biochemistry* 25:4478–4482 (1986).

Zaug et al., "A Labile Phosphodiester Bond at the Ligation Junction in a Circular Intervening Sequence RNA," *Science* 224:574–578 (1984).

SEQ ID NO. 12 — 13-mer: 5'-*pGGGAGUCAGGAUN-3'
SEQ ID NO. 8 — 12-mer: 5'-*pGGGAGUCAGGAU-3'

SEQ ID NO. 13 — 13-mer: 5'-pppGGG*AG(2'-FU)C*AGG*A(2'-FU)N-3' ⟶
SEQ ID NO. 14 — 12-mer: 5'-pppGGG*AG(2'-FU)C*AGG*A(2'-FU)-3' ⟶

7-mer : 5'-*pGGGAG(2'-NH2U)C-3'
6-mer : 5'-*pGGGAGU-3'

5' CACAACACUGAUGAGGCCGUUAGGCCCGAAACGGGCA 3'

SEQ ID NO. 15

MODIFIED RIBOZYMES

This is a division of application Ser. No. 07/965,411, filed Aug. 9, 1993, hereby incorporated by reference herein in totality, including drawings.

SPECIFICATION

Certain naturally occurring ribonucleic acids (RNAS) are subject to self-cleavage. The first reported example is the cleavage of the ribosomal RNA precursor of the protozoan Tetrahymena (for a review see Cech, Ann.Rev.Biochem. 59 (1990), 543–568) which requires guanosine as cofactor. A number of examples of RNA cleavage have been subsequently discovered in viroid, virusoid and satellite RNAs (for reviews see Sheldon et al. in Nucleic Acids and Molecular Biology (1990) Vol. 4, pg. 227–242, ed. F. Eckstein and D. M. J. Lilley, Springer Verlag Berlin Heidelberg; Symons, TIBS 14 (1989), 445–450). These cleavages involve site-specific breakage of a phosphodiester bond in the presence of a divalent cation such as $Mg^{2+}$, generating a 5'-hydroxyl and a 2',3',-cyclic phosphodiester terminus. Sequence analysis around the site of self-cleavage of several of such RNAs has led to the identification of a common structural feature essential for cleavage which was named a "hammerhead" structure (Hutchins et al., Nucleic Acids Res. 14 (1986) 3627–3640). This structure consists of three helices and 13 conserved nucleotides (framed in below scheme) which form a three dimensional structure amenable to cleavage at one particular position. The self-catalyzed cleavage is normally an intramolecular process, i.e. a single RNA molecule contains all the functions necessary for cleavage. However, Uhlenbeck (Nature 328 (1987), 596–600) has demonstrated that this hammerhead structure does not have to be embodied in one strand but can be made up of two strands. These two strands combine to form the hammerhead structure which leads to phosphodiester bond cleavage (indicated by an arrow) in one of the strands (strand S) whereas the other (strand E) remains unaltered and can participate in many cleavage reactions. This strand meets the definitions of an enzyme and is called a ribozyme. Whereas the framed sequences (below scheme) are conserved the others may vary provided that the structure of base paired and the single stranded regions remains intact.

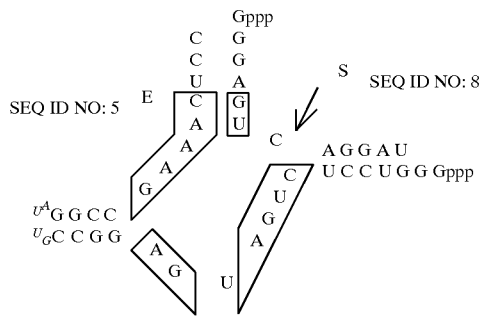

The cleavage reaction after the trinucleotide GUC has been studied in detail (Ruffner et al., Gene 82 (1989), 31–41; Fedor and Uhlenbeck, Proc.Natl.Acad.Sci. USA 87 (1990), 1668–1672). Ribozymes with new specificities have also been constructed (Haseloff and Gerlach, Nature 334 (1988), 585–591) indicating that cleavage can for example also take place after the sequences GUA, GUU, CUC, AUC and UUC.

Further examples for RNA enzymes are the hairpin RNA (Hampel et al., Nucleic Acids Res. 18 (1990), 299–304), as well as RNA containing proteins such as the telomerase (Greider and Blackburn, Nature 337 (1989), 331–337) and the RNase P (Baer et al., in Nucleic Acids and Molecular Biology (1988), Vol. 3, pp. 231–250, ed. F. Eckstein and D. M. J. Lilley, Springer Verlag, Berlin/Heidelberg).

Ribozymes are potentially of interest for use as therapeutic agents (for review see Rossi and Sarver, TIBTECH 8 (1990), 179–183). A possible strategy would be to destroy an RNA necessary for the expression of both foreign genes such as viral genes and particular endogenous genes. This requires the construction of a RNA molecule which is able to form a hammerhead or a hairpin structure with the target RNA and to cleave this at a predetermined position. A first application to the inhibition of the HIV-1 virus by this strategy has been reported (Sarver et al., Science 247 (1990), 1222–1224). Other examples of the action of targeted hammerhead ribozymes in vivo are Cammeron and Jennings (Proc.Natl.Acad.Sci. USA 86 (1986), 9139–9143) and in vitro Cotten et al. (Mol. Cell. Biol. 9 (1989), 4479–4487).

Further, other useful catalytic properties of ribozymes are known, e.g. dephosphorylase and nucleotidyl transferase activities (see Patent Application W088/04300). Therein RNA enzymes are disclosed which are capable of dephosphorylating oligonucleotide substrates with high sequence specificity, which distinguishes them from known protein enzymes. RNA molecules also can act as RNA polymerases, differing from protein enzymes in that they use an internal rather than an external template. Thus, various heteropolymers can be constructed by variant RNA enzyme forms. This enables the formation for example of messenger RNA molecules for particular proteins or peptides. Furthermore, Herschlag and Cech (Nature 344, (1990), 405–409) describe an RNA enzyme with DNase activity.

To be useful as a therapeutic agent the RNA enzyme has to be introduced into target cells. There are a priori two methods for delivery of the ribozyme into the target cells:

(a) exogenous delivery of a preformed synthetic RNA;
(b) endogenous transcription of a ribozyme-coding gene located on a plasmid.

A great disadvantage of method (a) resides in the very low stability of RNA molecules under physiological conditions due to their fast degradation by a variety of ribonuclease enzymes present in the living cell. The disadvantages of method (b) result from the great difficulties of specifically and stably inserting a ribozyme-coding gene into the cells of higher organisms. Furthermore, the problem of degradation also occurs with in vivo synthesized RNA molecules.

Therefore the problem underlying the present invention was to provide RNA molecules comprising both catalytic activities and enhanced stability against chemical and enzymatical degradation, which can be employed as therapeutical agents or as biocatalysts in biochemical or biotechnological processes.

It was however known from a recent paper by Perreault et al. (Nature 344 (1990), 565–567) that certain modifications of the RNA enzyme, e.g. the incorporation of 2'-deoxyribonucleotides at a few positions of a ribozyme lead to a great impairment of the catalytic activity.

It was now surprisingly found that certain chemical modifications at the 2'-position of the ribose sugar which enhance the stability of an RNA molecule do not considerably affect and/or abolish the catalytic properties of ribozymes.

Therefore it is an object of the present invention to provide an RNA molecule with catalytic activity comprising at least one modified nucleoside, wherein the hydroxy group at the 2'-position of the ribose sugar is replaced by a modifier group, selected from halo, sulfhydryl, azido, amino, monosubstituted amino and disubstituted amino groups.

The catalytic activity of an RNA molecule according to the present invention comprises advantageously at least one of the group consisting of nucleotidyl transferase, dephosphorylase, deoxyribonuclease and sequence specific endoribonuclease activities. Preferably the catalytic activity comprises a sequence specific endoribonuclease activity. More preferably the RNA is a hammerhead ribozyme as described above. Especially preferred is that the ribozyme can combine with another RNA strand to form a hammerhead structure consisting of two strands, wherein the modified RNA strand is the E strand as described above.

Although a hammerhead ribozyme is especially preferred, other RNA enzymes are encompassed also by the present invention, e.g. the Tetrahymena ribozyme (Cech, Ann.Rev..Biochem. 59 (1990), 543–568) in naturally occurring form or a shortened form thereof (Zang et al., Biochemistry 27 (1988), 8924–8931), and especially the Hairpin RNA (Hampel et al., Nucleic Acids Res. 18 (1990) 299–304) or RNA containing proteins such as the RNase P (Baer et al., in Nucleic Acids & Molecular Biology (1988), Vol. 3, pp 231–250, ed. F. Eckstein and D. M. J. Lilley, Springer Verlag Heidelberg), the telomerase (Greider and Blackburn, Nature 337 (1989), 331–337).

The incorporation of a modifier group at the 2'-position of the ribose sugar appears also to be particularly useful for RNA with new functions either derived at by a procedure that depends on alternate cycles of selection (Tuerk and Gold, Science 249 (1990), 505–510; Ellington and Szostak, Nature 346 (1990), 818–822) or any other method.

The modifier group replacing the hydroxy group at the 2'-position of the ribose sugar is selected from halo, sulfhydryl, azido, amino, monosubstituted amino, and disubstituted amino groups. The halo group can be a fluoro, chloro, bromo or iodo group, wherein the fluoro group is preferred. The substituents of the substituted amino group are preferably $C_1$–$C_3$ alkyl and or hydroxyalkyl groups. Most preferably the modifier group is a halo or an unsubstituted amino group.

The incorporation of a modifier group at the 2'-position of the ribose sugar significantly increases the RNA stability against enzymatic cleavage. It was confirmed that 2'-deoxy-2'-fluorouridine and 2'-deoxy-2'-aminouridine incorporated at specific positions of a ribozyme prevented cleavage at these positions by RNase A (see FIGS. 3+4). This enzyme cleaves at the 3'-position of pyrimidine nucleosides and requires the presence of the 2'-hydroxyl group (Uchida and Egami (1971), in The Enzymes Vol. IV, 3rd ed. (Ed. P. D. Boyer), Academic Press, pp. 205–250). Furthermore, results obtained with polynucleotides show that the presence of the 2'-amino function also slows down degradation by unspecific nucleases such as snake venom phosphodiesterase (Hobbs et al., Biochemistry 12 (1973), 5138–5145). The presence of a 2'-halogroup also inhibits nucleases such as DNase I (Hobbs et al., Biochemistry 11 (1972), 4336–4344). Results with polynucleotides also show that the presence of a halogen at the 2'-position of a nucleotide protects against the action of human serum nucleases (Black et al., Virology 48 (1972) 537–545). Thus, protection by incorporation of a modified ribose sugar according to the present invention will be rather general and not be restricted to RNases which depend on the presence of the 2'-hydroxyl group.

In a ribonucleic acid the ribose sugar is linked to a nucleotide base via a N-glycosidic bond. The nucleotide base, which is attached to the modified ribose sugar in an RNA molecule of the present invention is selected from the group consisting of bases naturally occurring in RNA and substituted bases. Preferably the modified ribose is attached to adenine, guanine, cytosine and/or uracil, which are the natural bases in RNA. The modified ribose, however, can also be attached to substituted bases, preferably selected from the group consisting of xanthine, hypoxanthine, 2,6-diamino purine, 2-hydroxy-6-mercaptopurine and purine bases substituted at the 6-position with sulfur or pyrimidine bases substituted at the 5-position with halo or $C_1$–$C_5$ alkyl groups, especially bromo or methyl groups. Most preferably the nucleotide base attached to the modified ribose sugar is uracil.

The modified nucleosides which are incorporated into a RNA molecule are either previously described compounds or compounds which can be prepared in analogy to known compounds. The mostly preferred fluoro and amino analogs of ribonucleosides have been described previously, 2'-deoxy-2'-fluorocytidine (Doerr & Fox, J.Org.Chem. 32 (1967), 1462; Mengel & Guschlbauer, Ang.Chem. 90 (1978), 557–558); 2'-deoxy-2'-fluoroadenosine (Ikehara & Miki, Chem.Pharm.Bull. 26 (1978), 2449–2453), 2'-deoxy-2'-fluorouridine (Codington et al., J.Org.Chem. 29 (1964), 558–564), 2'-deoxy-2'-aminouridine (Verheyden et al., J.Org.Chem. 36 (1971), 250) and 2'-deoxy-2-aminocytidine (Verheyden et al. (1971) supra). For the synthesis of some of these compounds more recent synthetic procedures can be employed. The 2'-deoxy-2'-fluorocytidine can be prepared from 2'-deoxy-2'-fluorouridine by the method of Sung (J.Org.Chem. 47 (1982), 3623–3628). The same method can be used for the transformation of 2'-deoxy-2'-azidouridine to 2'-deoxy-2'-azidocytidine (Verheyden et al. (1971), supra). The latter can be reduced to 2'-deoxy-2'-aminocytidine by the method of Mungall et al. (J.Org.Chem. 40 (1975), 1659).

The synthesis of the 2'-deoxy-2'-fluoronucleoside 5'-triphosphates can be carried out either according to Ludwig (Acta Biochim. et Biophys. Acad.Sci.Hung. 16 (1981), 131–133) or Ludwig and Eckstein (J.Org.Chem. 54 (1989), 631–635). The 2'-deoxy-2'-aminouridine and -cytidine 5'-triphosphates can be prepared as described for the diphosphates by Hobbs et al. (Biochemistry 12 (1973), 5138–5145) with the modification that pyrophosphate is employed instead of phosphate. The 2'-deoxy-2'-fluoronucleoside 3'-phosphoramidites for automated oligonucleotide synthesis can be prepared by the method of Sinha et al. (Nucleic Acids Res. 12 (1984), 4539–4557). For the synthesis of the corresponding 2'-amino derivatives, the amino group can be protected by trifluoroacetylation according to Imazawa and Eckstein (J.Org.Chem. 44 (1979), 2039–2041).

An RNA according to the present invention comprises at least one modified nucleoside, wherein the hydroxy group at the 2'-position of ribose is replaced by a modifier group. A preferred embodiment of the present invention is an RNA molecule wherein all nucleosides of one kind (i.e. adenosine or guanosine or cytidine or uridine) contain modified sugars, while the remaining three nucleosides contain unmodified sugars. More preferably the modified nucleoside is pyrimidine nucleoside, i.e. cytidine or uridine or a substituted derivative thereof. Most preferably the modified sugar is 2'-fluoro ribose or 2'-amino ribose. Examples for this embodiment are the hammerhead ribozymes E2 and E3, which were derived from a hammerhead ribozyme E1 described by Fedor and Uhlenbeck (Proc.Natl.Acad.Sci. USA 87 (1990), 1668–1672). In E2 all uridine residues are replaced by 2'-deoxy-2'-fluoro-uridine and in E3 all uridine residues are replaced by 2'-deoxy-2'-aminouridine residues. The ribozymes E2 and E3 show a ribonuclease activity which is comparable to that of the unmodified RNA molecule E1.

In a further preferred embodiment of the present invention all nucleosides of two different kinds contain modified sugars, while the remaining two nucleosides contain unmodified sugars. More preferably all pyrimidine nucleosides, i.e. cytidine and uridine (including substituted pyrimidine bases) contain modified sugars, most preferably 2'-fluoro or 2'-amino ribose derivatives.

Still a further embodiment of the present invention is an RNA molecule comprising a modification pattern (i.e. which nucleosides are modified and which are unmodified) which is designated as a so-called "selective modification pattern". An RNA comprising selective modification pattern is a molecule wherein nucleosides at specifically selected locations can be modified while nucleosides at other specifically selected locations can be unmodified. For instance, nucleotides which are known to be hypersensitive sites for ribonucleases (e.g. due to the secondary structure of the RNA molecule) should be modified to achieve an extended life time of the RNA molecule. An example for a ribonuclease-hypersensitive site is provided at position 21 of ribozyme E1. As shown in FIG. 3 the RNA molecule is cleaved at this position by RNase A with very high intensity.

Still a further embodiment of the present invention is a RNA molecule additionally comprising at least one modified internucleotidic phosphodiester linkage. Examples for suitable modified phosphodiester linkages are methyl phosphonate groups or phosphorothioate groups, the latter being especially preferred. Preferably at least the 5'-terminal phosphodiester linkage and/or the 3'-terminal phosphodiester linkage of the RNA molecule is modified. More preferably the 5'-terminal phosphodiester linkage and the last three 3'-terminal phosphodiester linkages are modified.

It was found, that the presence of modified internucleotidic linkages alone was not sufficient to provide increased stability against degradation. However, the combined presence of 2'-modified ribose sugars together with modified internucleotidic linkages showed an additive stability enhancing effect. A more than fifty-fold increase in stability conferred by both modifications outweighs the decreased efficiency in cleavage compared to a unmodified ribozyme.

The synthesis of RNA molecules having modified internucleotidic linkages is preferably accomplished by means of chemical synthesis as described below.

A further object of the present invention is a process for the synthesis of an RNA molecule with catalytic activity, comprising:

incorporating into an RNA chain at least one modified nucleoside, wherein the hydroxy group at the 2'-position of the ribose sugar is replaced by a modifier group, selected from halo, sulfhydryl, azido, amino, monosubstituted amino and disubstituted amino groups.

Preferably the modifier group is a halo (i.e. a fluoro, chloro, bromo or iodo group) or an amino group, more preferably a fluoro or an unsubstituted amino group. It should be noted, that the process of the present invention also comprises the synthesis of an RNA molecule wherein nucleotides with at least two different modifier groups (e.g. fluoro and amino groups) are incorporated.

There are preferably two approaches for the incorporation of these modified nucleotides into RNA. One is by automated chemical synthesis of RNA molecules which can be carried out on solid support or in solution, preferably with the respective phosphoramidites or H-phosphonates as nucleotide precursors, the other involves enzymatic incorporation by transcription of appropriate nucleic acid, preferably DNA templates with a nucleic acid polymerase using the 2'-modified nucleoside 5'-triphosphates. By means of automated chemical synthesis RNA molecules comprising modified internucleotidic linkages may be prepared by incorporating the corresponding chemically modified nucleotide precursors such as the methyl phosphonate derivatives into the RNA chain. For the incorporation of phosphorothioate linkages the standard phosphoramidite derivatives are used as nucleotide precursors. After the coupling of the precursor to the RNA chain has taken place the subsequent oxidation step, however, is not performed with iodine, as in the case of non-modified linkages, but with sulfur or a sulfurating agent, whereby the phosphorothioate group is obtained.

The chemical synthesis of modified RNA molecules is carried out in analogy to that of unmodified RNA or DNA molecules, which is known in the art. More specifically the RNA synthesis is carried out by chemical synthesis on solid support involving the stepwise addition of the respective nucleotide precursors. After having synthesized an RNA product of the desired length, the RNA is removed from the solid support by conventional means and purified, preferably by gel electrophoresis. Alternatively the chemical RNA synthesis can also be carried out by any other known technique without using a solid support. E.g. the RNA can be synthesized in a soluble form and subsequently purified by means known in the art.

When the 2'-amino modifier group is incorporated into the RNA chain it has to be protected before the phosphitylation reaction (i.e. the preparation of the nucleotide precursor) and for subsequent use in the coupling reactions. For this purpose the trifluoroacetyl group is preferably used as a protecting group, because it is stable during the cycles of synthesis on the nucleic acid synthesizer and is removable under the conventional treatment with ammonia.

Alternatively the synthesis of the RNA chain can be carried out by transcription from a nucleic acid template by an appropriate nucleic acid polymerase. Preferably the template is a DNA template and the nucleic acid polymerase is a DNA dependent RNA polymerase. More preferably the DNA dependent RNA polymerase is selected from the group consisting of T7, T3 and SP6 polymerases, which are highly processive bacteriophage RNA polymerases. Among these polymerases the T7 RNA polymerase is most preferred. The DNA template for the synthesis of a modified RNA molecule according to the present invention is preferably constructed by inserting a synthetic DNA fragment coding for the desired RNA sequence into an appropriate site of a plasmid, wherein said plasmid comprises a promoter for the respective RNA polymerase and said site is located at such a position of the plasmid, so that the synthetic DNA fragment can be transcribed from said promoter. The transcription reaction is advantageously carried out as a run off transcription. Alternatively, synthetic DNA fragments may serve as transcription templates without a plasmid portion. Those fragments, however, should contain a transcription start signal, which allows an effective RNA synthesis.

The polymerisation of 2'-deoxy-2'-halo nucleotides, e.g. 2'-deoxy-2'-fluorouridine, -cytidine, -adenosine, -guanosine and the respective chloro compounds, is preferably carried out by T7 polymerase in the presence of $Mn^{2+}$ ions as cofactor. Alternatively, the polymerisation of 2'-aminonucleotides, e.g., 2'-deoxy-2'-aminouridine 2'-deoxy-2'-aminocytidine, 2'-deoxy-2'-aminoadenosine, and 2'-deoxy-2'-aminoguanosine, is preferably carried out in the presence of $Mg^{2+}$ ions as cofactor.

From the experimental data of the following examples it is evident that the presence of 2'-deoxy-2'-fluorouridine and 2'-deoxy-2'-aminouridine in a hammerhead ribozyme do not abolish catalytic activity. This is qualitatively shown in FIG. 3 for the presence of the 2'-fluorouridine in the substrate part and quantitatively in Table 1 for various other enzyme/substrate pairs. It is true that all the modifications resulted in an increase in the $K_m$-value which was most pronounced for the amino substitution. However, this perturbation of the active structure lies well within the range of Km variation observed for hammerhead systems with different base composition (Fedor & Uhlenbeck, supra). In addition, very surprisingly the incorporation of a single 2'-aminouridine immediately 5' of the site of cleavage in the substrate increased the kcat markedly (table 1), so that it is conceivable to produce ribozymes of enhanced activity by the selective introduction of 2'-modified-nucleosides at specific sites. These results definitely show that there is no requirement for the presence of 2-hydroxyl groups throughout the enzyme part of the hammerhead structure for catalytic activity but that the modifications according to the present invention are tolerated at least in certain positions. In contrast, the incorporation of only 15% 2'-deoxynucleotides into a hammerhead ribozyme is reported to decrease the catalytic efficiency by two orders of magnitude, while not affecting the $k_m$ (Perreault et al. (1990), supra). Since the rate of cleavage is determined by the angle of attack of the 2'-hydroxyl on the phosphorus at the site of cleavage, it is greatly influenced by the overall structure of the hammerhead system. Thus, the observed influence of 2'-modifications on the rate supports the notion that the 2'-fluoro analogs adopt a structure more similar to that of ribonucleotides than that of deoxyribonucleotides. This apparently also holds for the amino analogs. The other 2'-modified nucleosides according to the present invention exhibit similar catalytic activity.

A still further object of the present invention is the use of RNA molecules with catalytic activity comprising at least one modified nucleotide, as therapeutic agents, especially for the specific cleavage of viral or other foreign genetic material or transcripts from viral or other foreign genetic material, or as biocatalyst in biochemical or biotechnological processes. For these purposes the RNA molecules of the present invention seem to be more suitable than their unmodified analogs, because of their increased stability against chemical and/or enzymatical cleavage.

The present invention shall be further illustrated by the following examples in combination with FIGS. 1–7. These examples however are not intended to narrow the scope of the present invention.

EXAMPLES

Figure 1A:
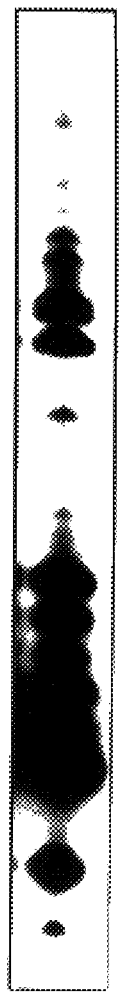
FIG. 1 shows autoradiographs of T7 RNA polymerase run off transcripts of the plasmid pUCRS after PAGE.

Example 1
Preparation of oligoribonucleotides

Automated synthesis of oligoribonucleotides: Automated oligoribonucleotide synthesis was carried out with an Applied Biosystems 380B DNA Synthesizer on a 1 μmol scale using the monomeric ribonucleotide phosphoramidites supplied by Milligen/Biosearch. Control pore glass columns with the ribonucleoside coupled to it were either from Milligen/Biosearch or Peninsula. The oligomers were worked up according to the specifications of the supplier of the ribonucleotide phosphoramidites (Milligen/Biosearch). After removal of the protecting groups the oligoribonucleotides were concentrated by spin dialysis on Amicon filter membranes centricon 10 and ethanol precipitated. The dried pellets were taken up in 50 μl water and subjected to PAGE. Bands were visualized by UV shadowing, cut out and the RNA was isolated by eluting at 37° C. overnight in buffer (0.25M ammonium acetate, 10 mM TRIS/HCl pH 8.0, 1 mM EDTA) (Fedor & Uhlenbeck, PNAS USA 87 (1990), 1668–1672). Concentrations were determined using the extinction coefficient per nucleotide of 6600 $M^{-1}cm^{-1}$ given in the literature (Fedor & Uhlenbeck 1990). Aqueous solutions of the oligoribonucleotides were stored at –20° C.

Construction of plasmids containing templates for run off transcription:

The following oligodeoxynucleotides were synthesized for the plasmid construction by the phosphoramidite method with an Applied Biosystems 380B DNA synthesizer:

RS2-T, 5'-d(GATATCCTGACTCCCTATAGTGAGTCGTATTA)-3' SEQ ID NO: 1;

RS2-C, 5'-d(TAATACGAC-TCACTATAGGGAGTCAGGATATCTGCA)-3' SEQ ID NO: 2;

RE1-T, 5'-d(GGAGTTTCGGCCTAACGGCC-TCATCAGAGGACCCTATAGTGAGTCGTATTA)-3' SEQ ID NO: 3 and RE2-C, 5'-d(TAATACGACTCACT-ATAGGGTCCTCTGATGAGGCCGTTAGGCCGAAA-CTCCTGCA)-3' SEQ ID NO: 4.

Preparation of ribozyme pUCRS and pUCRE16 clones:

The commercially available plasmid pUC19 was cleaved in a one step reaction using the restriction enzymes Iso-SacI and PstI. The DNA was then purified by 2% agarose gel electrophoresis followed by electroelution using a Centricon 30 and the centroelution apparatus supplied by Amicon. The oligonucleotide primer pairs, RE1-T and RE2-C (ribozyme enzyme), or RS2-T and RS2-C (ribozyme substrate) were phosphorylated as previously described (Taylor et al., Nucleic Acids Res. 13 (1985), 8749–8764). These oligonucleotide pairs were used for cloning of the T7 promotor along with either the DNA sequence for the ribozyme yielding pUCRE16 or the ribozyme substrate yielding pUCRS according to the procedure of King & Blakesley (Focus 8 (1986), 1–3). After transformation of competent cells (Olsen & Eckstein, PNAS USA 87 (1990), 1451–1456) white colonies were screened for the presence of a second AvaII site in the case of the pUCRE16 or a unique EcoRV site for pUCRS. The sequence of the purified double-stranded DNA from each clone was determined by the procedure of Olsen and Eckstein (Nucleic Acids Res. 17 (1989), 9613–9620).

T7 RNA polymerase run off transcripts:

T7 RNA polymerase run off transcripts were synthesized on a 150 µl to 500 µl scale by adapting the procedure given by Milligan and Uhlenbeck (Meth. in Enzymology 180A (1989), 51–62). Transcription reactions were run in 40 mM TRIS pH 8.0, 1 mM spermidine, 5 mM DTT, 0.01% Triton x-100, 20 mM $MgCl_2$, 2.5 mM nucleotides, 200 nM DNA template, 0.2 U/µl human placental RNAse inhibitor, and 100 U/µl T7 RNA polymerase. When 2'-deoxy-2'-fluoronucleoside triphosphates were employed, the $MgCl_2$ was replaced by 20 mM $MnCl_2$. Reactions were run at 37° C. for 3 hours. Transcripts were purified by PAGE as described above. Aqueous solutions of the oligoribonucleotides were stored at −20° C.

Figure 1B:
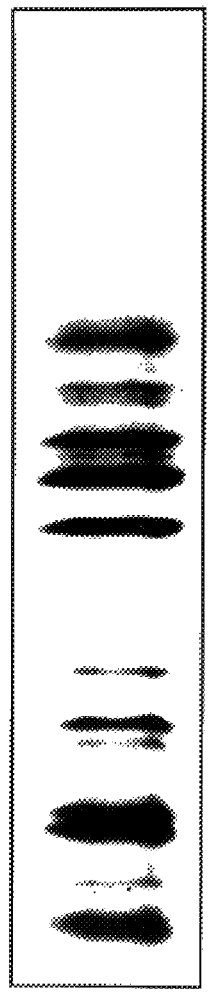

FIG. 1 shows autoradiographs of T7 RNA polymerase run off transcriptions of pUCRS after PAGE. A: The transcription was performed on a 150 µL scale in the presence of 20 mM $MgCl_2$ and 2.5 mM each of the four nucleoside triphosphates at 37° C. for 3 h. The reaction mixture was dephosphorylated with alkaline phosphatase and 5'-$^{32}$P-labeled by reaction-with polynucleotide kinase and [γ-$^{32}$P]-ATP. The labeled transcription mixture was subjected to PAGE. B: The transcription was performed on a 150 µL scale at 37° C. for 3 h in the presence of 20 mM $MnCl_2$, 0.5 mM ATP, 25 µCi [α-$^{32}$P]-ATP, 2.5 mM CTP and GTP, and 2.5 mM 2'-fluorouridine triphosphate. The transcription mixture was directly subjected to PAGE. The asterisks mark $^{32}$P-labeled phosphates. 'N' denotes any nucleotide added by T7 RNA polymerase beyond the full length of the template DNA (c. f. Milligan and Uhlenbeck, Meth.in Enzymology 180A (1989), 51–62).

Figure 2:
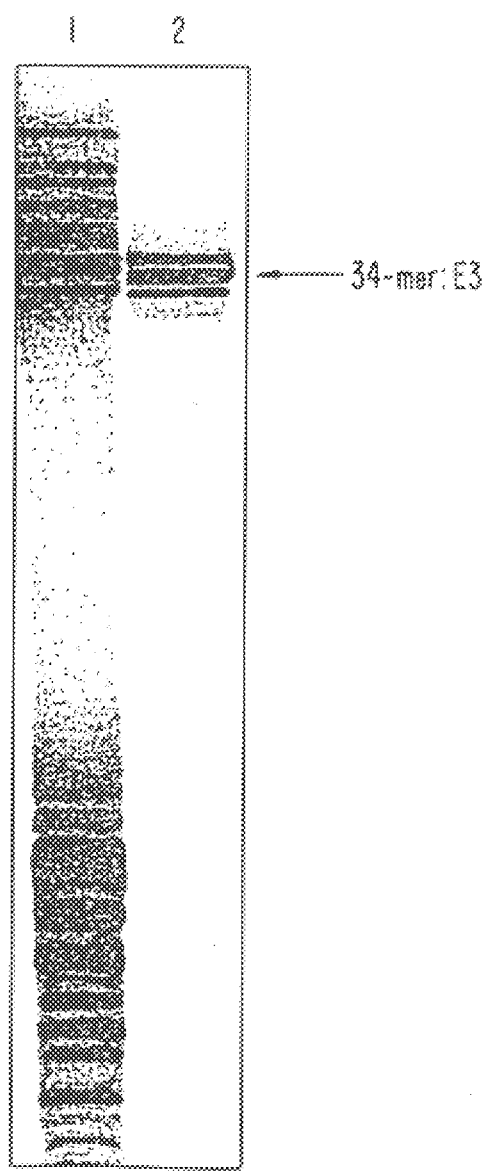
FIG. 2 shows an autoradiograph of T7 RNA polymerase run off transcripts of the plasmid pUCRE containing 2'-aminouridine after PAGE.

FIG. 2 shows an autoradiograph of T7 RNA polymerase run off transcripts of pUCRE 16 containing 2'-aminouridine after PAGE. Lane 1: 2'-aminouridine containing 34-mer marker E3, synthesized chemically. Lane 2: The transcription was performed on a 150 µl scale at 37° C. for 3 h in the presence of 20 mM $MgCl_2$, 60 µCi [α-$^{32}$P]ATP, 1 mM CTP and GTP, and 1 mM 2'-aminouridine triphosphate. The transcription mixture was directly applied PAGE.

Preparation of oligoribonucleotides: The following oligoribonucleotides were prepared a.) by run off transcription (sequences given without the 5'-triphosphate):

E1, 5'-GGGUCCUCUGAUGAGGCCGUUAGG-CCGAAACUCC-3' SEQ ID NO: 5;

E2, 5'-GGG(2'-FU)CC(2'-FU)C(2'-FU)GA(2'-FU)GAGGCCG(2'-FU)(2'-FU)AGGCCGAAAC(2'-FU)CC-3' SEQ ID NO: 6 and E3, 5'-GGG(2'-$NH_2$U)CC(2'-$NH_2$U)C(2'-$NH_2$U)GA(2'-$NH_2$U)GAGGCCG(2'-$NH_2$U)(2'-$NH_2$U)AGGCCGAAAC(2'-$NH_2$U)CC-3' SEQ ID NO: 7;

S1, 5'-GGGAGUCAGGAU-3' SEQ ID NO: 8; S3, 5'-GGGAG(2'-FU)CAGGA(2'-FU)-3' SEQ ID NO: 9 and

S4, 5'-GGGAGU(2'-FC)AGGAU-3' SEQ ID NO: 10.

b.) by chemical synthesis: The oligoribonucleotides E1, E2, E3, S1 and S2, 5'-GGGAG(2'-$NH_2$U)CAGGAU-3' SEQ ID NO: 11.

5'-$^{32}$P-labeling of oligoribonucleotides:

Oligoribonucleotides obtained from run off transcriptions were dephosphorylated by treatment with RNAse free bovine alkaline phosphatase, purified by Quiagen tip-20 columns according to the protocol given by the manufacturer (Diagen Inc.) and treated with T4 polynucleotide kinase and γ-$^{32}$P-ATP. Labeled oligoribonucleotides were purified by PAGE.

Example 2

Digestion of oligoribonucleotides with RNase A

Partial digestion of oligoribonucleotides with RNase A: The oligoribonucleotides E1 and E2 were subjected to RNase A digestion after 5'-$^{32}$P labeling according to the procedure of Donis-Keller et al. (Nucleic Acids Res. 4 (1977), 2527–2538) with the following changes. Approximately 25 µmoles of 5'-$^{32}$P-labeled RNA was added to 50 µl buffer containing 7M urea, 50 mM EDTA, 0.04% bromophenol blue, 0.04% xylene cyanol FF and 0.25 mg/ml tRNA on ice. The RNA was then equally divided into 5 labeled tubes, heated to 50° C. for 5 min and then immediately placed on ice. Ribonuclease A, 2 µl ($2\times10^{-4}$ units), was added to the first tube and mixed using the pipette. The enzyme was then successively 5 fold diluted into three additional tubes using a new pipette tip after each transfer from one tube to the next. The fifth tube was a control sample to which no enzyme was added. All tubes were then incubated at 50° C. for 5 min, placed on ice and analysed by PAGE.

Total degradation of oligoribonucleotides by RNAse A: The oligoribonucleotides S1 and S2 were digested with RNase A after 5'-$^{32}$P labeling according to the following protocol: The oligomer (8.5 µM in a final volume of 20 µl) was reacted with $1.25\times10^{-3}$ Units of RNAse A in buffer containing 50 mM TRIS/HCl pH 7.5 and 10 mM $MgCl_2$ for 10 min at 37° C. Products were analyzed by PAGE.

Figure 3:
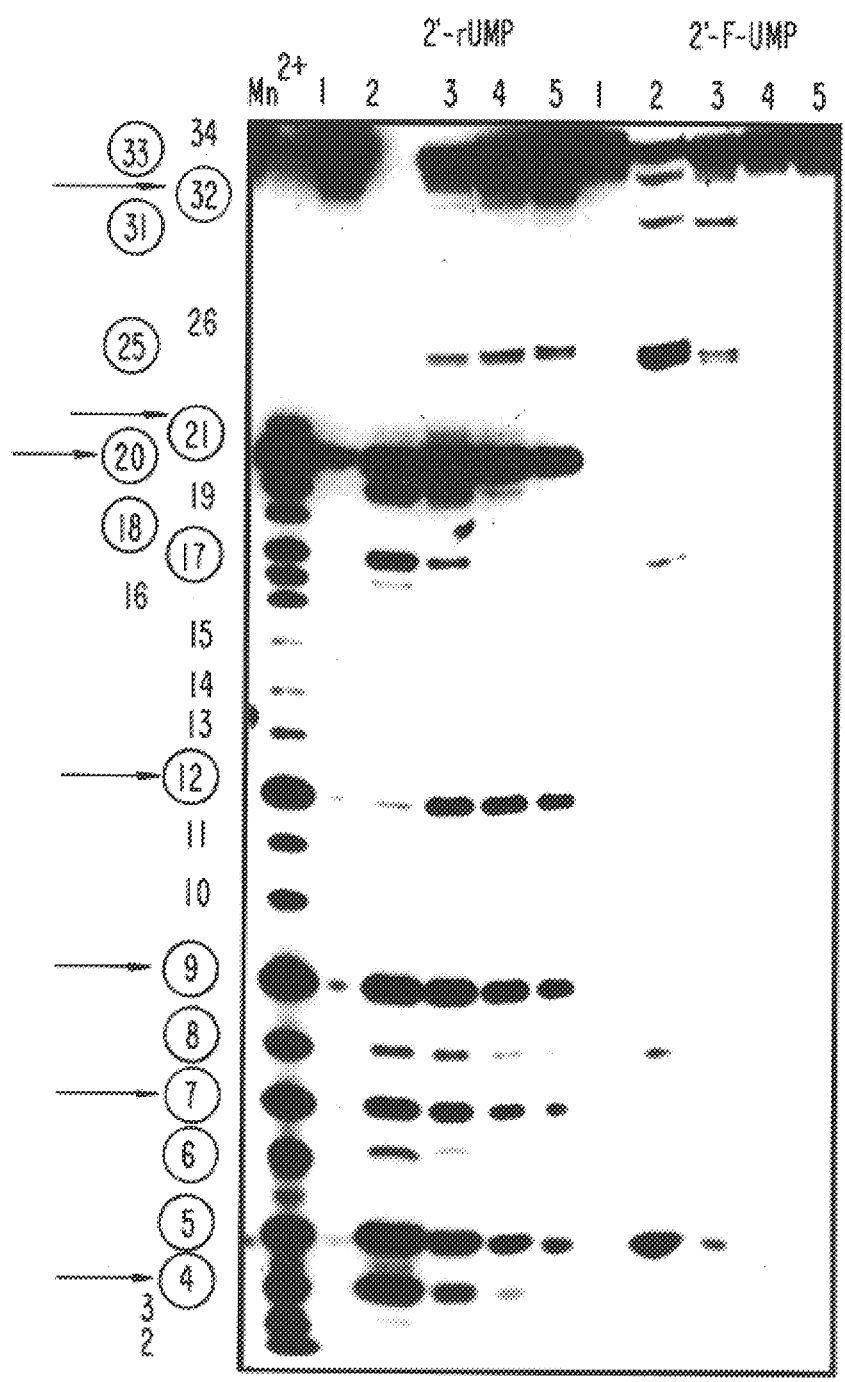
FIG. 3 shows an autoradiograph of partial Ribonuclease A cleavage of 5'-labeled run off transcripts E1 and E2 separated by PAGE.

FIG. 3 shows an autoradiograph of partial Ribonuclease A cleavage of 5'-labeled run off transcripts E1 and E2 separated by PAGE. Conditions as described before. The numbered lanes correspond to 1) no enzyme added, 2) $2\times10^{-4}$ units RNase A, 3) $3\times10^{-5}$ units RNase A, 4) $8\times10^{-6}$ units RNase A, 5) $16\times10^{-7}$ units RNase A. Base numbering was facilitated by counting the bands of a $Mn^{2+}$ mediated cleavage of the unmodified transcript (10 µmoles RNA heated to 90° C. for 3 min in 10 mM $MnCl_2$). The circled numbers indicate the bands expected from RNase-A susceptible cleavage positions. Arrows indicate the bands that arise from cleavage 3' to uridine and which are absent in the lanes where 2'-fluorouridine containing ribozyme was cleaved.

Figure 4:
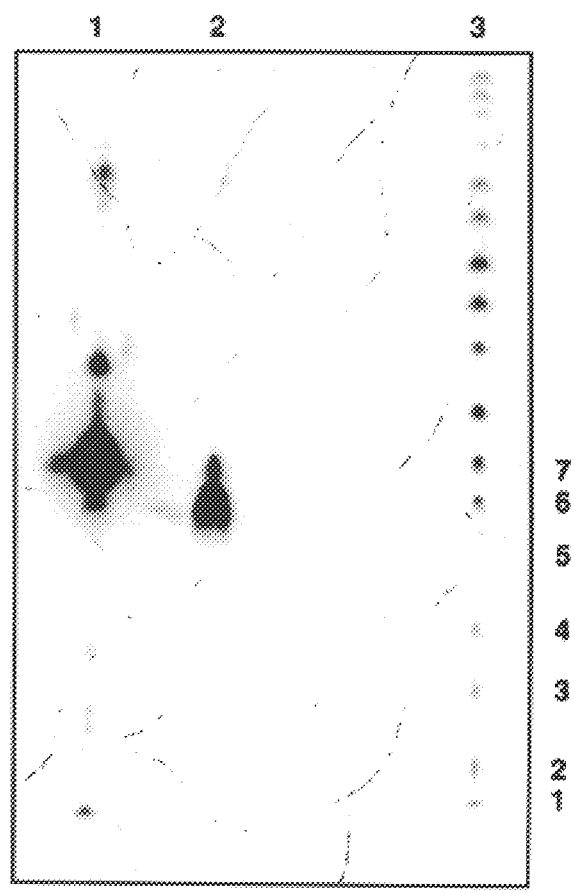
FIG. 4 shows an autoradiograph of the total degradation of S1 and S2 by RNase A.

FIG. 4 shows an autoradiograph of the total degradation of S1 and S2 by RNase A after PAGE. Details of the reaction are as described above. Lane 1: total digestion of 12-mer S2; lane 2: total digestion of 12-mer S1; lane 3: cleavage ladder of the 34-mer E1 by reaction with 20 mM $MnCl_2$ at 90° C. for 3 min as a length standard. The product of cleavage of S2 is 1 nucleotide longer than that of S1 indicating the presence of 2'-aminouridine at position 6.

Example 3

Cleavage of oligoribonucleotide substrates by ribozymes

Determination of cleavage kinetics: The cleavage reactions were performed by a procedure adapted from Fedor and Uhlenbeck (1990), supra). Stock solutions of the ribozyme enzyme (typically 20 µL final volume, 100 nM final concentration, 50 mM TRIS/HCl, pH 7.5) and substrate oligonucleotide (typically 40 µl, 2 µM final concentration) were heated separately at 90° C. for 1 min and cooled to room temperature for 15 min prior to the addition of divalent metal ion ($MnCl_2$ or $MgCl_2$, 10 mM final concentration). These stocks were incubated separately at 25° C. for 15 min prior to initiation of the cleavage reactions. The reactions were started by adding enzyme to substrate (50 mM TRIS/HCl, pH 7.5, 20 µl final volume, $MgCl_2$, 10 mM final concentration), with typical concentrations of 10 nM enzyme and between 50 and 5000 nM substrate. At set times 10 µl aliquots were transferred into 10 µl urea stop mix and subjected to PAGE. Autoradiographs were analyzed on an LKB ULTROSCAN XL laser densitometer.

Figure 5:
FIG. 5 shows an autoradiograph of the cleavage of 2'-fluorouridine and $^{32}$p-AMP containing substrate S3 by ribozyme E1.

In the investigated hammerhead ribozyme system a 12-mer substrate oligonucleotide (designated as S) is cleaved by a 34-mer enzyme oligonucleotide (designated as E) at the 3'-position of cytidine-7 as indicated by the arrow in the structure in the Introduction. This cleavage generates a heptamer with a 2'-3'-cyclic phosphate terminus (product 1) and a pentamer with a 5'-hydroxyl terminus (product 2) (Ruffner et al, Gene 82 (1989), 31–41). We observed these types of cleavage products not only with the oligoribonucleotides E1 and S1, but also with the 2'-fluorouridine-containing substrate S3 (FIG. 5). As expected, the substrate oligonucleotide S4, containing a 2'-fluorocytidine at the position of cleavage was not cleaved under identical conditions. These two reactions contained 2'-fluorouridine in the substrate oligonucleotide.

However, potentially more interesting for future applications is the question whether the presence of this modification in the enzyme part of the ribozyme will interfere with its catalytic activity. Thus, the reaction of the 2'-fluorouridine-containing ribozyme E2 with the unmodified substrate S1 was investigated. Indeed, the gel analysis indicated that the substrate was cleaved with similar efficiency as the pair E1 and S1. The catalytic constants of the 2'-fluorouridine-containing ribozyme E2 were determined (FIG. 6) and compared to those of the unmodified ribozyme E1. This comparison reveals that the second order rate constant for the former ($k_{cat}/K_m$=0.0026 $nM^{-1}$) is one order of magnitude smaller than that of the latter ($k_{cat}/K_m$=0.023 $nM^{-1}$) (Fedor & Uhlenbeck (1990), supra) (Table 1). This decrease in catalytic efficiency is primarily due to a decrease in the rate of cleavage, whereas the Km values for both ribozymes is nearly identical. This reduced rate of cleavage, however, lies well within the range of cleavage efficiencies observed for various hammerhead systems with different base compositions (Fedor & Uhlenbeck (1990), supra). Hammerhead ribozyme reactions can be carried out with $MgCl_2$ as well as with $MnCl_2$ as metal ion cofactor, where the half life of cleavage is decreased in the presence of the latter cofactor by about 10 fold (Uhlenbeck, Nature 328 (1987), 596–609). Such a decrease in the half life of the substrate under cleavage conditions upon switching from $Mg^{2+}$ to $Mn^{2+}$ was also observed for the reaction of 2'-fluorouridine-containing enzyme E2 with substrate S1. Thus the metal ion requirement for the cleavage reaction is not altered by the incorporation of 2'-fluoronucleotide analogs.

The effect of the presence of 2'-aminouridine in the ribozyme was also investigated. When the 2'-aminouridine containing ribozyme E3 is reacted with nonmodified substrate S1, the catalytic efficiency drops an order of magnitude to $k_{cat}/K_m$=0.0015 $nM^{-1}$. This decrease in efficiency is clearly due to a higher $K_m$, while the $k_{cat}$ remains almost unaltered. Thus, the overall efficiency of the 2'-aminouridine ribozyme is comparable to the one of the 2'-fluorouridine containing ribozyme. In the complementary reaction of the nonmodified ribozyme E1 with the selectively 2'-aminouridine modified substrate S2 the catalytic efficiency is increased compared to the above reaction to $k_{cat}/K_m$=0.0063 $nM^{-1}$. This effect is entirely due to an increase in $k_{cat}$. This trend is even more pronounced in the reaction of the 2'-aminouridine containing ribozyme E3 with S2, where the catalytic efficiency is increased to $k_{cat}/K_m$= 0.011 $nM^{-1}$, again mainly due to an increased $k_{cat}$. The kinetic parameters for all of the above reactions are summarized in Table 1.

TABLE 1

Kinetic constants of 2'-modified nucleotide-containing ribozymes.[a]

| Enzyme | Substrate | $k_{cat}$ ($min^{-1}$) | $K_m$ (nM) | $k_{cat}/K_m$ ($nM^{-1}$ $min^{-1}$) |
|---|---|---|---|---|
| E1 (nonmod.) | S1 (nonmod.) | 3.0 | 140 | 0.023 |
| E2 (2'-FU) | S1 (nonmod.) | 0.8 | 300 | 0.0026 |
| E3 (2'-$NH_2U$) | S1 (nonmod.) | 2.3 | 1500 | 0.0015 |
| E3 (2'-$NH_2U$) | S2 (2'-$NH_2U$) | 19.0 | 1800 | 0.011 |
| E1 (nonmod.) | S2 (2'-$NH_2U$) | 10.0 | 1600 | 0.0063 |

[a]Kinetic constants were determined from Eadie-Hofstee plots of cleavage reactions run with 10 nM ribozyme and with substrate concentrations ranging from 50 nM to 1200 nM.

Thus, the herein compiled kinetic data shows that while the cleavage efficiency of 2'-fluoro- and 2'-aminouridine modified ribozyme is somewhat reduced, it is still within the range of variations observed for hammerhead systems of different base composition. It also becomes evident that it is possible to increase the catalytic efficiency by selectively introducing 2'-modifications at specific positions. While the latter effect was demonstrated for the substrate oligoribonucleotide, it is anticipated that a similar influence on catalysis can be found for selective modifications in the enzyme.

FIG. 5 shows an autoradiograph of the cleavage of 2'-fluorouridine and $^{32}$P-AMP-containing substrate S3 by ribozyme E1. The cleavage reaction was performed in the presence of 10 mM $MgCl_2$ in 50 mM TRIS/HCl, pH 7.5 on a 40 μl scale at 25° C. The concentration of E1 and S3 was 2.5 μM and 7.5 μM, respectively. All other details are as described above (c.f. Determination of Cleavage Kinetics). At the indicated times 10 μl aliquots were transferred into 10 μl water and 10 μl urea stop mix prior to PAGE. Lane 1: reaction after 0.5 min; lane 2: reaction after 15 min; lane 3: reaction after 30 min. The asterisks mark $^{32}$P-labeled phosphates.

Figure 6:
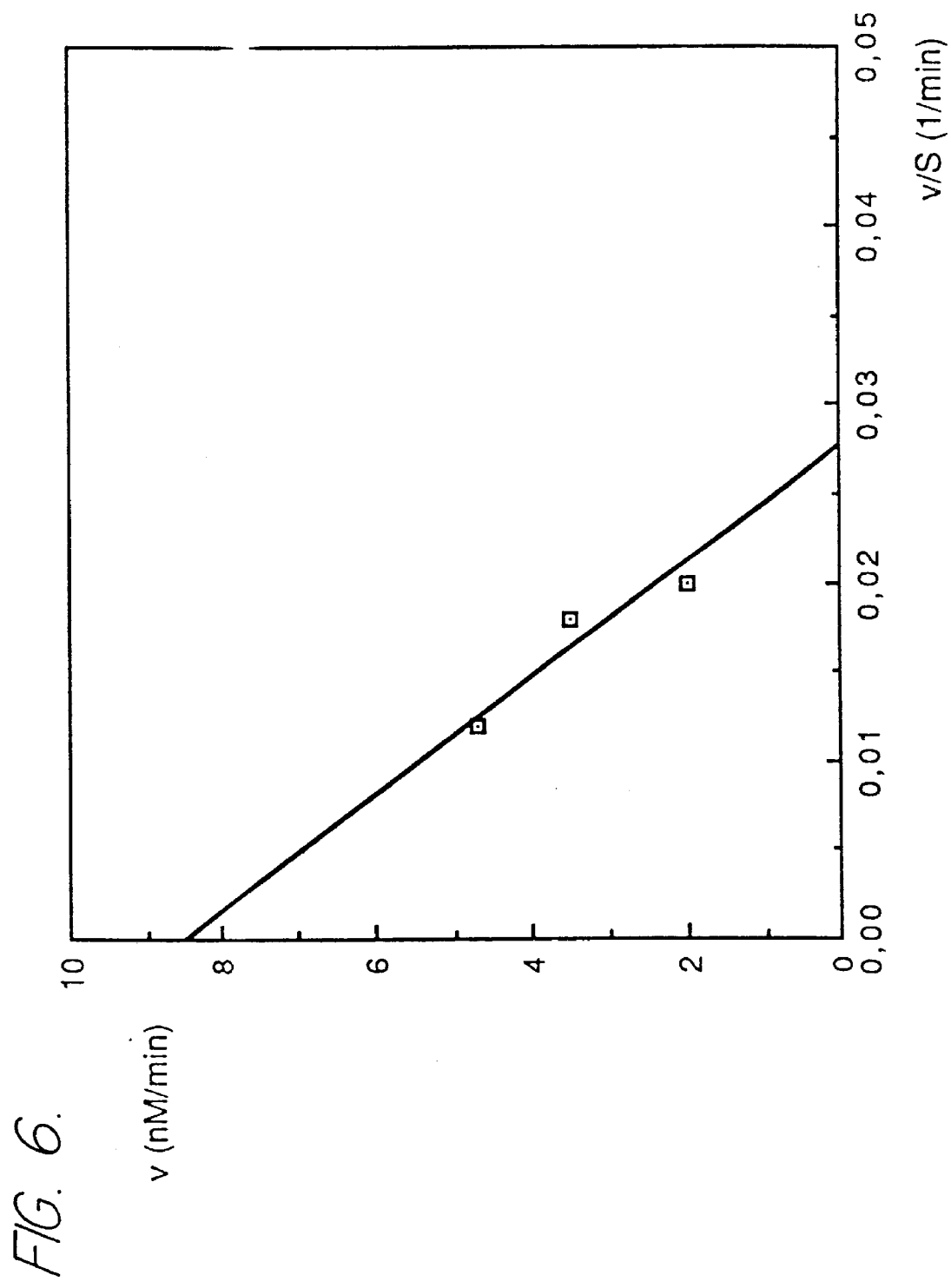
FIG. 6 shows an Eadie-Hofstee plot of the ribozyme reaction of E2 with S1.

FIG. 6 shows an Eadie-Hofstee plot of the ribozyme reaction of E2 with S1. The cleavage reaction were performed on a 20 μl scale in the presence of 10 mM $MgCl_2$ with a 10 nM concentration of E2 and concentrations of S1 of 50 nM, 100 nM, 200 nM, 400 nM, 500 nM, and 700 nM. After 7 min 10 μl aliquots were transferred into 10 μl water and 10 μl urea stop mix prior to PAGE. It was established previously that these time points fall within the linear range of initial velocities. The autoradiographs were evaluated by integration of their optical density on a laser densitometer.

Figure 7:
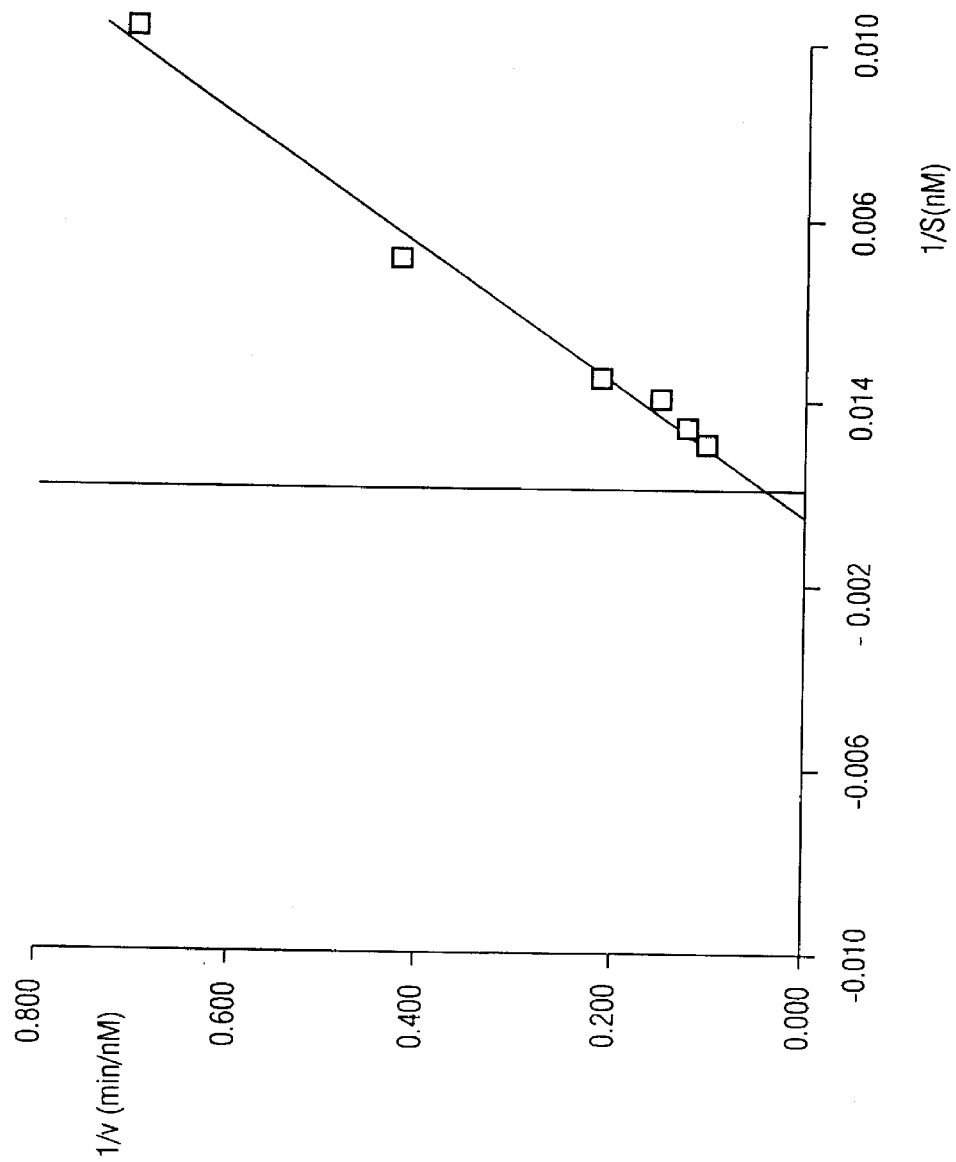
FIG. 7 shows an Lineweaver-Burk plot of the ribozyme reaction of E3 with S1.

FIG. 7 shows an Lineweaver-Burk plot of the ribozyme reaction of E3 with S1. The cleavage reactions were performed on a 20 μl scale in the presence of 10 mM $MgCl_2$ with a 10 nM concentration of E3 and concentrations of S1 of 50 nM, 100 nM, 200 nM, 400 nM, 500 nM and 700 nM. All other details are as in FIG. 6.

Example 4

Cleavage of HIV-1 LTR RNA using ribozymes

Figures 8, 9:
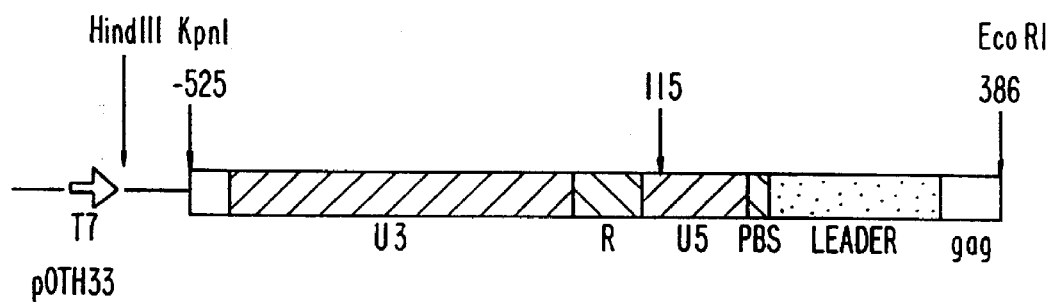
FIG. 8 shows the organisation of the HIV-1 sequence cloned into pOTH33.
FIG. 9 shows the nucleotide sequence of the ribozyme RE115 SEQ ID NO: 15.

Plasmid Construction: A plasmid, pOTH33, was constructed by cloning the HIV-1 sequence from position −525 to 386 (according to the sequence numbering by Ratner et al., Nature 313 (1985), 277–284) into the commercially available plasmid pSPT19 (Pharmacia). The HIV sequence is under transcriptional control of a T7 promotor (T7). A diagrammatic view of the HIV insertion in pOTH33 is given in FIG. 8. The HIV-1 LTR region consists of the U3 region, the R region and the U5 region. It is flanked on its 5'-end by the polypurine tract and on tis 3'-end by the primer binding site (PBS), the leader sequence and a part of the gag gene. The arrows at position −525 and 386 indicate the restriction sites used for the construction of pOTH33. The arrow at position 115 shows the site for ribozyme mediated cleavage.

RNA of HIV-1 from position −525 to 386 comprising the long terminal repeat sequence from nucleotide −453 to 182 was obtained by run-off transcription of EcoRI cleaved plasmid pOTH33 (100 ng/µl DNA template, 10 mM DTT, 500 µM of each rNTP, 50 mM Tris-Cl pH 7.5, 2 mM spermidine, 6 mM MgCl$_2$, 2 µCi/µl [α-$^{32}$P]-ATP, 50 U/µl RNase inhibitor and 15 U/µl T7 RNA polymerase, 2 h at 4° C.) and subsequent incubation of the reaction mix with DNaseI (1 U/µl, 10 min at 37° C.) (RNase free) and phenol-chloroform extraction. The obtained RNA was designated as LTR RNA.

Position 115 of the HIV-1 LTR RNA containing the potential cleavage site GUC was chosen as a target for ribozyme catalyzed cleavage. Hammerhead ribozymes targeted against this site were chemically synthesized. The nucleotide sequence of the unmodified hammerhead enzyme RE115 is given in FIG. 9.

Cleavage Kinetics with LTR RNA: $k_{cat}/K_m$ values were determined under single turnover conditions. Ribozymes were preincubated at 75° C. for 1 min in the presence of 50 mM Tris-Cl pH 7.5 followed by 5 min of incubation at 37° C. MgCl$_2$ was added to a final concentration of 10 mM and the solutions were again incubated for 5 min at 37° C. LTR RNA was directly used as an aqueous solution. The reaction mixture (10 µl) contained between 20 nM and 1 µM ribozyme, 50 mM Tris-Cl pH 7.5 and 10 mM MgCl$_2$. The reaction was started by addition of LTR RNA to a final concentration of 10 nM. After 1 hour at 37° C. the reaction was stopped by addition of 10 µl stop mix and analysed by 4% PAGE (40 cm long, 8M urea). After 1 h electrophoresis at 50 W followed by autoradiography the fraction of non-cleaved LTR RNA was determined by laser scanning densitometry. $k_{cat}/K_m$ values were obtained by plotting the remaining fraction of LTR RNA (Frac S) against the ribozyme concentration ([RE]) according to the following equation:

$$k = \frac{\ln(FracS)}{t} = [RE]\frac{k_{cat}}{K_m},$$

where k is the observed reaction rate and t is the reaction time of 1 h.

In order to investigate the influence of chemical modifications on the catalytic efficiency of a ribozyme several analogs of RE115 containing 2'-fluoro or 2'-deoxy substitutions and/or terminal phosphorothioate linkages were synthesized. Whereas 2'-fluorocytidine substitutions has no effect on the catalytic efficiency [Table 2, RE115(FC)], 2'-fluorouridine substitutions caused a fivefold decrease of $k_{cat}/K_m$ [Table 2, RE115(FU)]. One 5'-terminal phosphorothioate group in combination with three 3'-terminal phosphorothioate groups diminished the catalytic efficiency only negligibly [Table 2, RE115(S)]. The same was true for the combination of terminal phosphorothioate linkages together with 2'-fluorouridine substitutions, where no further decrease in $k_{cat}/K_m$ as observed [Table 2, RE115(FU),S)]. Substituting all pyrimidine ribonucleotides by their 2'-fluoro analogs and introducing the four phosphorothioate linkages decreased the catalytic efficiency only seven-fold compared to the unmodified ribozyme [Table 2, RE115(FC,FU,S)]. In contrast substitutions of all pyrimidine ribonucleotides by their 2'-deoxynucleoside analogs combined with phosphorothioates resulted in a decrease of $k_{cat}/K_m$ by factor of 50 [Table 2, RE115(dC,dU,S)]. Thus, RE115(dC,dU,S) is some 7 times less efficient than RE115(FC,FU,S).

TABLE 2

Influence of chemical modifications on the Cleavage of LTR RNA by RE115

| Ribozyme | $k_{cat}/K_m$, M$^{-1}$ s$^{-1}$ | $k_{cat}/K_m$, relative |
|---|---|---|
| RE115 | 500 | 1 |
| RE115(S) | 360 | 0,72 |
| RE115(FC)[1] | 490 | 0,98 |
| RE115(FU)[1] | 89 | 0,18 |
| RE115(FU,S)[1] | 59 | 0,12 |
| RE115(FC,FU,S)[1] | 69 | 0,14 |
| RE115(dC,dU,S)[2] | 10 | 0,020 |

[1]Examples of the present invention
[2]Comparative example

Example 5

Stability of oligoribonucleotides

The ribozymes of Example 4 were examined for their stability against nuclease digestion.

Test conditions:

Molt 4 clone 8 cells (kindly supplied by E. Jurkiewicz, Deutsches Primatenzentrum, Göttingen) grown in medium RMPI 1640 to a cell density of about 10$^6$ cells/ml were centrifuged at 1000 g for 5 min in a Heraeus Minifuge. 5'-$^{32}$P-labeled ribozymes were pre-heated for 1 min at 90° C., chilled on ice, added to the cell supernatant to a final concentration of 300 nM and incubated at 37° C. Aliquots were taken at the indicated time points and analysed by 20% PAGE containing 8M urea followed by autoradiography.

Results:

More than 80% of RE115 was degraded after 2 min incubation in the cell supernatant as indicated by denaturing PAGE. For RE115(S) similar results were obtained. However, no degradation of RE115(FC,FU,S) within 1 hour was observed. A comparison with the rate of degradation of the unmodified ribozyme indicates that the combination of 2'-modified pyrimidine nucleosides and terminal phosphorothioate linkages results in an estimated increase of more than fifty-fold of ribozyme stability against digestion by nucleases present in T cell supernatant. 2'-modified ribozymes without phosphorothioate group show a stability which is about two times lower than the stability of RE115 (FC,FU,S).

We claim:
1. A method of using an RNA molecule having catalytic activity as a therapeutic agent or biocatalyst, wherein said RNA molecule comprises at least one modified nucleoside, wherein the hydroxy group at the 2'-position of the ribose sugar is replaced by a modifier group, selected from halo, azido, amino, monosubstituted amino and disubstituted amino groups.

2. A therapeutic agent comprising as active ingredient an RNA molecule with catalytic activity comprising at least one modified nucleoside, wherein the hydroxy group at the 2'-position of the ribose sugar is replaced by a modifier group, selected from halo, azido, amino, monosubstituted amino and disubstituted amino groups, wherein said RNA is optionally together with convenient fillers, adjuvants, carriers and diluents.

3. A process of preparing a therapeutic agent, wherein the therapeutic agent comprises as active ingredient an RNA molecule with catalytic activity comprising at least one modified nucleoside, wherein the hydroxy group at the 2'-position of the ribose sugar is replaced by a modifier group, selected from halo, azido, amino, monosubstituted amino and disubstituted amino groups, wherein said RNA is optionally together with convenient fillers, adjuvants, carriers and diluents.

4. The method of claim 1, wherein said modifier group is a fluoro group.

5. The method of claim 1, wherein said modifier group is an amino group.

6. The method of claim 1, wherein said RNA molecule is in a hammerhead configuration.

7. The method of claim 1, wherein said RNA molecule is in a hairpin configuration.

8. The method of claim 1, wherein said catalytic activity of said RNA molecule comprises a sequence-specific endoribonuclease activity.

9. The method of claim 1, wherein said modified ribose sugar is attached to a nucleotide base, and said base is selected from a group consisting of bases naturally occurring in RNA and substituted bases.

10. The method according to claim 9, wherein said substituted nucleotide base is selected from a group consisting of xanthine, hypoxanthine, 2,6-diamino purine, 2-hydroxy-6-mercaptopurine and purine bases substituted at the 6-position with sulfur or pyrimidine bases substituted at the 5-position with halo or $C_1$–$C_5$ alkyl groups.

11. The method of claim 1, wherein said RNA comprises the nucleotide sequence E2 (SEQ ID NO. 6):

5'-GGG(2'-FU)CC(2'-FU)C(2'-FU)GA(2'-FU) GAGGCCG(2'-FU)(2'-FU)AGGCCGAAAC(2'-FU) CC-3'; and wherein 2'-FU represents 2'-deoxy-2'-fluorouridine monophosphate.

12. The method of claim 1, wherein said RNA comprises the nucleotide sequence E3 (SEQ ID NO. 7):

5'-GGG(2'-NH$_2$U)CC(2'-NH$_2$U)C(2'-NH$_2$U)GA(2'-NH$_2$U)GAGGCCG(2'-NH$_2$U)(2'-NH$_2$U) AGGCCGAAAC(2'-NH$_2$U)CC-3'; and wherein 2'-NH$_2$U represents 2'-deoxy-2'-aminouridine monophosphate.

13. The method of claim 1, wherein said RNA molecule further comprises at least one modified internucleotidic phosphodiester linkage.

14. The method of claim 13, wherein at least the 5'-terminal phosphodiester linkage of said RNA molecule is modified.

15. The method of claim 13, wherein at least the 3'-terminal phosphodiester linkage of said RNA molecule is modified.

16. The method of claim 13, wherein the 5'-terminal phosphodiester linkage and the 3'-terminal phosphodiester linkages of said RNA molecule are modified.

17. The therapeutic agent of claim 2, wherein said modifier group comprises a fluoro group.

18. The therapeutic agent of claim 2, wherein said modifier group comprises an amino group.

19. The therapeutic agent of claim 2, wherein said RNA is in a hammerhead configuration.

20. The therapeutic agent of claim 2, wherein said RNA is in a hairpin configuration.

21. The therapeutic agent of claim 2, wherein said catalytic activity of said RNA molecule comprises a sequence-specific endoribonuclease activity.

22. The therapeutic agent of claim 2, wherein said modified ribose sugar of said RNA molecule is attached to a nucleotide base, and said base is selected from a group consisting of bases naturally occurring in RNA and substituted bases.

23. The therapeutic agent of claim 22, wherein said substituted nucleotide base is selected from a group consisting of xanthine, hypoxanthine, 2,6-diamino purine, 2-hydroxy-6-mercaptopurine and purine bases substituted at the 6-position with sulfur or pyrimidine bases substituted at the 5-position with halo or $C_1$–$C_5$ alkyl groups.

24. The therapeutic agent of claim 2, wherein said RNA molecule comprises the nucleotide sequence E2 (SEQ ID NO. 6):

5'-GGG(2'-FU)CC(2'-FU)C(2'-FU)GA(2'-FU) GAGGCCG(2'-FU)(2'-FU)AGGCCGAAAC(2'-FU) CC-3'; and wherein 2'-FU represents 2'-deoxy-2'-fluorouridine monophosphate.

25. The therapeutic agent of claim 2, wherein said RNA comprises the nucleotide sequence E3 (SEQ ID NO. 7):

5'-GGG(2'-NH$_2$U)CC(2'-NH$_2$U)C(2'-NH$_2$U)GA(2'-NH$_2$U)GAGGCCG(2'-NH$_2$U)(2'-NH$_2$U) AGGCCGAAAC(2'-NH$_2$U)CC-3'; and wherein 2'-NH$_2$U represents 2'-deoxy-2'-aminouridine monophosphate.

26. The therapeutic agent of claim 2, wherein said RNA molecule further comprises at least one modified internucleotidic phosphodiester linkage.

27. The therapeutic agent of claim 26, wherein at least the 5'-terminal phosphodiester linkage of said RNA molecule is modified.

28. The therapeutic agent of claim 26, wherein at least the 3'-terminal phosphodiester linkage of said RNA molecule is modified.

29. The therapeutic agent of claim 26, wherein the 5'-terminal phosphodiester linkage and the 3'-terminal phosphodiester linkages of said RNA molecule are modified.

30. The process of claim 3, wherein said modifier group comprises a fluoro group.

31. The process of claim 3, wherein said modifier group comprises an amino group.

32. The process of claim 3, wherein said RNA molecule is in a hammerhead configuration.

33. The process of claim 3, wherein said RNA molecule is in a hairpin configuration.

34. The process of claim 3, wherein said catalytic activity of said RNA molecule comprises a sequence-specific endoribonuclease activity.

35. The process of claim 3, wherein said modified ribose sugar of said RNA molecule is attached to a nucleotide base, and said base is selected from a group consisting of bases naturally occurring in RNA and substituted bases.

36. The process of claim 35, wherein said substituted nucleotide base is selected from a group consisting of xanthine, hypoxanthine, 2,6-diamino purine, 2-hydroxy-6-mercaptopurine and purine bases substituted at the 6-position with sulfur or pyrimidine bases substituted at the 5-position with halo or $C_1$–$C_5$ alkyl groups.

37. The process of claim 3, wherein said RNA molecule comprises the nucleotide sequence E2 (SEQ ID NO. 6):

5'-GGG(2'-FU)CC(2'-FU)C(2'-FU)GA(2'-FU)GAGGCCG(2'-FU)(2'-FU)AGGCCGAAAC(2'-FU)CC-3'; and wherein 2'-FU represents 2'-deoxy-2'-fluorouridine monophosphate.

38. The process of claim 3, wherein said RNA comprises the nucleotide sequence E3 (SEQ ID NO. 7):

5'-GGG(2'-$NH_2$U)CC(2'-$NH_2$U)C(2'-$NH_2$U)GA(2'-$NH_2$U)GAGGCCG(2'-$NH_2$U)(2'-$NH_2$U)AGGCCGAAAC(2'-$NH_2$U)CC-3'; and wherein 2'-$NH_2$U represents 2'-deoxy-2'-aminouridine monophosphate.

39. The process of claim 3, wherein said RNA molecule further comprises at least one modified internucleotidic phosphodiester linkage.

40. The process of claim 39, wherein at least the 5'-terminal phosphodiester linkage of said RNA molecule is modified.

41. The process of claim 39, wherein at least the 3'-terminal phosphodiester linkage of said RNA molecule is modified.

42. The process of claim 39, wherein the 5'-terminal phosphodiester linkage and the 3'-terminal phosphodiester linkages of said RNA molecule are modified.

* * * * *

SEQUENCE LISTING ( 1 ) GENERAL INFORMATION:

( i i i ) NUMBER OF SEQUENCES: 15

( 2 ) INFORMATION FOR SEQ ID NO: 1:

( i ) SEQUENCE CHARACTERISTICS:
        ( A ) LENGTH: 32
        ( B ) TYPE: nucleic acid
        ( C ) STRANDEDNESS: single
        ( D ) TOPOLOGY: linear ( i i ) SEQUENCE DESCRIPTION: SEQ ID NO: 1:

GATATCCTGA CTCCCTATAG TGAGTCGTAT TA        32

( 2 ) INFORMATION FOR SEQ ID NO: 2:

( i ) SEQUENCE CHARACTERISTICS:
        ( A ) LENGTH: 36
        ( B ) TYPE: nucleic acid
        ( C ) STRANDEDNESS: single
        ( D ) TOPOLOGY: linear ( i i ) SEQUENCE DESCRIPTION: SEQ ID NO: 2:

TAATACGACT CACTATAGGG AGTCAGGATA TCTGCA        36

( 2 ) INFORMATION FOR SEQ ID NO: 3:

( i ) SEQUENCE CHARACTERISTICS:
        ( A ) LENGTH: 51
        ( B ) TYPE: nucleic acid
        ( C ) STRANDEDNESS: single
        ( D ) TOPOLOGY: linear ( i i ) SEQUENCE DESCRIPTION: SEQ ID NO: 3:

GGAGTTTCGG CCTAACGGCC TCATCAGAGG ACCCTATAGT GAGTCGTATT A        51

( 2 ) INFORMATION FOR SEQ ID NO: 4:

( i ) SEQUENCE CHARACTERISTICS:
        ( A ) LENGTH: 55
        ( B ) TYPE: nucleic acid
        ( C ) STRANDEDNESS: single
        ( D ) TOPOLOGY: linear ( i i ) SEQUENCE DESCRIPTION: SEQ ID NO: 4:

TAATACGACT CACTATAGGG TCCTCTGATG AGGCCGTTAG GCCGAAACTC CTGCA        55

( 2 ) INFORMATION FOR SEQ ID NO: 5:

( i ) SEQUENCE CHARACTERISTICS:
        ( A ) LENGTH: 34
        ( B ) TYPE: nucleic acid
        ( C ) STRANDEDNESS: single
        ( D ) TOPOLOGY: linear ( i i ) SEQUENCE DESCRIPTION: SEQ ID NO: 5:

GGGUCCUCUG AUGAGGCCGU UAGGCCGAAA CUCC        34

( 2 ) INFORMATION FOR SEQ ID NO: 6:

( i ) SEQUENCE CHARACTERISTICS:
        ( A ) LENGTH: 34
        ( B ) TYPE: nucleic acid
        ( C ) STRANDEDNESS: single
        ( D ) TOPOLOGY: linear ( i x ) FEATURE:
   ( D ) OTHER INFORMATION: The letter "N" stands for
      2'- fluorouridine.

( i i ) SEQUENCE DESCRIPTION: SEQ ID NO: 6:

GGGNCCNCNG ANGAGGCCGN NAGGCCGAAA CNCC        34

( 2 ) INFORMATION FOR SEQ ID NO: 7:

( i ) SEQUENCE CHARACTERISTICS:
      ( A ) LENGTH: 34
      ( B ) TYPE: nucleic acid
      ( C ) STRANDEDNESS: single
      ( D ) TOPOLOGY: linear ( i x ) FEATURE:
      ( D ) OTHER INFORMATION: The letter "N" stands for
         2'- aminouridine.

( i i ) SEQUENCE DESCRIPTION: SEQ ID NO: 7:

GGGNCCNCNG ANGAGGCCGN NAGGCCGAAA CNCC        34

( 2 ) INFORMATION FOR SEQ ID NO: 8:

( i ) SEQUENCE CHARACTERISTICS:
      ( A ) LENGTH: 12
      ( B ) TYPE: nucleic acid
      ( C ) STRANDEDNESS: single
      ( D ) TOPOLOGY: linear ( i i ) SEQUENCE DESCRIPTION: SEQ ID NO: 8:

GGGAGUCAGG AU        12

( 2 ) INFORMATION FOR SEQ ID NO: 9:

( i ) SEQUENCE CHARACTERISTICS:
      ( A ) LENGTH: 12
      ( B ) TYPE: nucleic acid
      ( C ) STRANDEDNESS: single
      ( D ) TOPOLOGY: linear ( i x ) FEATURE:
      ( D ) OTHER INFORMATION: The letter "N" stands for
         2'- fluorouridine.

( i i ) SEQUENCE DESCRIPTION: SEQ ID NO: 9:

GGGAGNCAGG AN        12

( 2 ) INFORMATION FOR SEQ ID NO: 10:

( i ) SEQUENCE CHARACTERISTICS:
      ( A ) LENGTH: 12
      ( B ) TYPE: nucleic acid
      ( C ) STRANDEDNESS: single
      ( D ) TOPOLOGY: linear ( i x ) FEATURE:
      ( D ) OTHER INFORMATION: The letter "N" stands for
         2'- fluorocytidine.

( i i ) SEQUENCE DESCRIPTION: SEQ ID NO: 10:

GGGAGUNAGG AU        12

( 2 ) INFORMATION FOR SEQ ID NO: 11:

( i ) SEQUENCE CHARACTERISTICS:
      ( A ) LENGTH: 12
      ( B ) TYPE: nucleic acid
      ( C ) STRANDEDNESS: single (D) TOPOLOGY: linear (ix) FEATURE:
    (D) OTHER INFORMATION: The letter "N" stands for
        2'- aminouridine.

(ii) SEQUENCE DESCRIPTION: SEQ ID NO: 11:

GGGAGNCAGG AU                                      12

(2) INFORMATION FOR SEQ ID NO: 12:

(i) SEQUENCE CHARACTERISTICS:
        (A) LENGTH: 13
        (B) TYPE: nucleic acid
        (C) STRANDEDNESS: single
        (D) TOPOLOGY: linear (ix) FEATURE:
        (D) OTHER INFORMATION: The letter "N" stands
            for one or more A, T, G, C.

(ii) SEQUENCE DESCRIPTION: SEQ ID NO: 12:

GGGAGUCAGG AUN                                    13

(2) INFORMATION FOR SEQ ID NO: 13:

(i) SEQUENCE CHARACTERISTICS:
        (A) LENGTH: 13
        (B) TYPE: nucleic acid
        (C) STRANDEDNESS: single
        (D) TOPOLOGY: linear (ix) FEATURE:
        (D) OTHER INFORMATION: Internal N stands for
            2'- fluorouridine.
            3'terminal N stands for
            one or more modified or
            unmodified nucleotides.

(ii) SEQUENCE DESCRIPTION: SEQ ID NO: 13:

GGGAGNCAGG ANN                                    13

(2) INFORMATION FOR SEQ ID NO: 14:

(i) SEQUENCE CHARACTERISTICS:
        (A) LENGTH: 12
        (B) TYPE: nucleic acid
        (C) STRANDEDNESS: single
        (D) TOPOLOGY: linear (ix) FEATURE:
        (D) OTHER INFORMATION: The letter "N" stands for
            2'- fluorouridine.

(ii) SEQUENCE DESCRIPTION: SEQ ID NO: 14:

GGGAGNCAGG AN                                      12

(2) INFORMATION FOR SEQ ID NO: 15:

(i) SEQUENCE CHARACTERISTICS:
        (A) LENGTH: 36
        (B) TYPE: nucleic acid
        (C) STRANDEDNESS: single
        (D) TOPOLOGY: linear (ii) SEQUENCE DESCRIPTION: SEQ ID NO: 15:

CACAACACUG AUGAGGCCGU UAGGCCGAAA CGGGCA        36